(12) United States Patent  (10) Patent No.: US 7,066,038 B2
Moir et al.  (45) Date of Patent: Jun. 27, 2006

(54) MATERIAL STABILITY TEST SYSTEM

(75) Inventors: Peter Donald Moir, Dungarvan (IE);
Nigel McSweeney, Dublin (IE)

(73) Assignee: Amebis Intellectual Properties Limited, County Waterford (IE)

( * ) Notice: Subject to any disclaimer, the term of this patent is extended or adjusted under 35 U.S.C. 154(b) by 0 days.

(21) Appl. No.: 10/964,734

(22) Filed: Oct. 15, 2004

(65) Prior Publication Data

US 2005/0145048 A1 Jul. 7, 2005

Related U.S. Application Data

(63) Continuation of application No. PCT/IE03/00056, filed on Apr. 15, 2003.

(51) Int. Cl.
*G01N 17/00* (2006.01)
(52) U.S. Cl. .................................... 73/865.6
(58) Field of Classification Search ............... 73/865.6, 73/866; 374/45, 57
See application file for complete search history.

(56) References Cited

U.S. PATENT DOCUMENTS

| 4,559,824 | A | | 12/1985 | Soma et al. | |
|---|---|---|---|---|---|
| 4,618,776 | A | * | 10/1986 | Sturm et al. | 250/372 |
| 5,610,344 | A | * | 3/1997 | Ueda et al. | 73/865.6 |
| 5,627,749 | A | * | 5/1997 | Waterman et al. | 702/6 |
| 5,915,838 | A | * | 6/1999 | Stals et al. | 374/45 |
| 6,536,289 | B1 | * | 3/2003 | Borowczak et al. | 73/809 |
| 6,738,697 | B1 | * | 5/2004 | Breed | 701/29 |
| 6,759,862 | B1 | * | 7/2004 | Kou | 374/45 X |
| 6,817,238 | B1 | * | 11/2004 | Go Boncan et al. | 73/865.6 X |
| 6,986,294 | B1 | * | 1/2006 | Fromme et al. | 73/866 X |
| 2001/0027688 | A1 | * | 10/2001 | Yamanaka | 73/865.6 |
| 2004/0083833 | A1 | * | 5/2004 | Hitt et al. | 73/866 |

FOREIGN PATENT DOCUMENTS

| DE | 41 05 440 A1 | 8/1992 |
|---|---|---|
| DE | 299 22 758 U1 | 3/2000 |
| DE | 199 15 906 A1 | 10/2000 |
| EP | 0 875 292 A1 | 11/1998 |
| EP | 1 013 326 A2 | 6/2000 |
| WO | WO-01/31316 A1 | 5/2001 |

* cited by examiner

*Primary Examiner*—Thomas P. Noland
(74) *Attorney, Agent, or Firm*—Birch, Stewart, Kolasch & Birch, LLP

(57) ABSTRACT

A material stability test system has a plurality of sealed test containers mounted in an environmental chamber. Each container has a humidifier for generating a desired humidity within the container. The environmental chamber is operable to provide a desired temperature within the environmental chamber. A test sample is mounted in each container. A sensor unit on each container senses the temperature and humidity within the container. An associated datalogger unit on each container connected to the sensor unit collects and transmits sensed temperature and humidity data at timed intervals via radio link to a remote monitoring station including a pc for recordal and/or display.

15 Claims, 4 Drawing Sheets

MATERIAL STABILITY TEST SYSTEM

This application is a Continuation of co-pending PCT International Application No. PCT/IE03/00056 filed on Apr. 15, 2003, which designated the United States, and on which priority is claimed under 35 U.S.C. § 120, which claims priority under 35 U.S.C. § 119(a) on Patent Application No(s). S002/0268 filed in Ireland on Apr. 15, 2002, the entire contents of which are hereby incorporated by reference.

BACKGROUND OF THE INVENTION

1. Field of the Invention

This invention relates to material stability testing and in particular to testing and monitoring the stability of samples such as chemicals, foods or food additives, biocides, agrochemicals and especially pharmaceuticals.

2. Discussion of the Background

During product development an integral part of the physiochemical characterisation of substances such as food additives, drugs or other materials development is the collection of large amounts of data on the stability of the material being developed. Typical examples of stability tests include those testing the effects of relative humidity and/or a temperature on a product. Such testing is especially relevant in the pharmaceutical industry where huge numbers of different compounds must be tested during all stages of product development. Drugs in early development are usually only available in small amounts and are expensive, limiting the quantities that can be used for stability studies.

Conventional methods for testing humidity and/or temperature include the use of relatively large humidity cabinets or rooms. Such methods are very expensive in a number of aspects. The cost of setting up tests using such systems can run into hundreds of thousands of euro for the initial capital outlay and maintenance costs. This can represent significant costs for many small to medium sized firms.

Some conventional stability testing methods involve placing materials in open petri dishes and placing the petri dishes in humidity cabinets or rooms. In this way a number of samples are tested together under the same conditions. However, when problems occur with the equipment the whole batch result is nullified. Also, dealing with open petri dishes is not suitable for toxic substances. Furthermore, the set humidity in the cabinet is disturbed upon opening of the cabinet in order to study the materials being tested or when inserting or removing individual samples.

Other methods, such as placing the samples in glass cabinets or jars containing saturated salts which generate a humid atmosphere may take up to two days to set up a range of samples under different conditions. Also the climate conditions within the cabinet or jar cannot be checked without adversely affecting the test. Setting up a range of saturated salts and the range of samples to cover various tests is slow and cumbersome using this type of standard laboratory equipment. Because of this, the drug developer will usually only set up the most essential and significant test limiting the amount of information that could be generated in early development.

Another problem often encountered is a degradant showing up in the stability trials after key milestones of product development have been reached, such as clinical studies. The changing to a more stable drug formulation at any of these stages is very costly and critical in the current age of quickness of the market.

Another type of material stability test kit and method is described in our previous patent application PCT/IE00/00135 (Publication No. WO 01/31316).

It is an object of the present invention to provide an improved material stability test system which overcomes the aforementioned problems.

SUMMARY OF THE INVENTION

According to the invention there is provided a material stability test system, including:
  a sealable test container for reception of a test sample of a material to be stability tested,
  means for sensing a climate condition within the test container when the test container is sealed in use, and
  data storage means in communication with the sensing means for recording measured values of said sensed climate condition.

The sensed climate condition may include one or more of various selected climate parameters such as temperature and relative humidity. In a particularly preferred embodiment means is provided for generating a desired climate condition within the test container. In a preferred embodiment each container is of a type described in our previously filed patent application no. PCT/IE00/00135 (Publication No. WO 01/31316) the contents of which are incorporated herein by reference.

Advantageously the material stability test system of the invention allows continuous monitoring of climate conditions during testing of the material without interfering with the test conditions. The data storage means or data collection means collects test data for analysis and review.

In one embodiment the data storage means is mounted on the test container. Information collected and stored locally, can be downloaded for review as required by the user.

In a further embodiment of the invention the data storage means is separate from the test container and a data transfer means is provided for communicating the measured value of the sensed climate condition to said remote data storage means.

Both local and remote data storage means may be provided if required.

In another embodiment means is provided for generating a unique identifier associated with the test container or test sample with means for associating said identifier with the sensed climate condition data prior to communicating the identifier and associated sensed climate condition data together to the data storage means.

In another embodiment the test container has a data transmitter for transmitting data by means of a radio signal to the data storage means.

In further embodiments the sensing means and/or the data transfer means are demountably engagable with the test container.

In a particularly preferred embodiment the sensing means and/or the data transfer means are mounted on a removable cover of the test container.

In another embodiment the sensing means and the data transfer means are mounted on a removable cover of the test container.

In another embodiment a two-part cover is provided for the test container, namely an inner cover part and an outer cover part, said inner cover part being engagable with the container to seal the container, the sensing means having sensors which are mounted on an inside face of the inner cover part, the outer cover part being engagable with the inner cover part, the data transfer means being mounted on the outer cover part, a connector being provided on one cover part for complementary engagement with an associated port on the other cover part for interconnecting the sensing means and the data transfer means.

In a further embodiment the inner cover part has a cap body having a top with a downwardly detending skirt having threads on an internal bore of the skirt for engagement with associated threads at an upper end of the test container, the sensors being mounted on an inside face of the top of the cap body.

In another embodiment the outer cover part has a body with a downwardly open socket for reception of the top of the cap body of the inner cover part, an inwardly extending rib being provided at a mouth of the socket for engaging and gripping an exterior of the skirt of the cap body to interengage the two cover parts.

In a further embodiment the data transfer means has a processor which is connected to a radio frequency transceiver with an associated antenna and battery power supply.

In another embodiment there is provided a material stability test system, including sensing means for sensing one or more selected material stability test parameters, means for mounting the sensing means on a test container for exposure to the same test conditions as a material stability test sample placed within the test container, data storage means, the sensing means being in communication with the data storage means for recording measured values of sensed material stability test parameters.

In another embodiment there is provided a material stability test system, including a sealable test container for reception of a test sample of a material to be stability tested, means for sensing a climate condition within the test container when the test container is sealed in use, data storage means in communication with the sensing means for recording measured values of said sensed climate condition, and means for generating a desired climate condition within the container.

In a further embodiment there is provided a material stability test system, including a sealable test container for reception of a test sample of a material to be stability tested, means for sensing a climate condition within the test container is sealed in use, data storage means in communication with the sensing means for recording measured values of said sensed climate condition, means for generating a desired climate condition within the test container, the data storage means being separate from the container and a data transfer means being provided for communicating the measured values of the sensed climate condition to said remote data storage means, the data transfer means including a data transmitter for transmitting data by means of a radio signal to the data storage means.

In another embodiment the invention provides a material stability test system including a sealable test container for reception of a test sample of a material to be stability tested, means for sensing a climate condition within the test container when the test container is sealed in use, data storage means in communication with the sensing means for recording measured values of said sensed climate condition, means for generating a desired climate condition within the test container, the data storage means being separate from the test container and a data transfer means being provided for communicating the measured values of the sensed climate condition to said remote data storage means, the data transfer means including a data transmitter for transmitting data by means of a radio signal to the data storage means, the sensing means and the data transfer means being mounted on a removable cover of the test container, said cover being of two-part construction, namely an inner cover part and an outer cover part, said inner cover part being engagable with the container to seal the container, the sensing means having sensors which are mounted on an inside face of the inner cover part, the outer cover part being engagable with the inner cover part, the data transfer means being mounted on the outer cover part, a connector being provided on one cover part for complementary engagement with an associated port on the other cover part for interconnecting the sensing means and the data transfer means.

In a further embodiment a display means, such as a VDU for example, is provided for display of data collected in the data storage means.

In another embodiment an environmental chamber is provided for reception of a plurality of separate test containers. Preferably said environmental chamber has means for controlling the temperature within the chamber.

In a further embodiment a first internal radio antenna is mounted within the environmental chamber to facilitate collection of data from test containers mounted within the environmental chamber in use, said first radio antenna being connected to an external radio frequency base station located outside the environmental chamber for communication of information between an interior and an exterior of the environmental chamber, said base station having means for communication with the data storage means.

In another aspect the invention provides a material stability test method, including:
mounting a test sample in a test container,
closing and sealing the test container,
generating desired test conditions within the container,
sensing the test conditions and communicating sensed values of the test conditions to a data storage means.

Ideally the method includes generating a desired climate condition within the sealed container. Preferably the method includes sensing the test conditions at selected time intervals.

BRIEF DESCRIPTION OF THE DRAWINGS

The invention will be more clearly understood by the following description of some embodiments thereof given by way of example only with reference to the accompanying drawings wherein.

DETAILED DESCRIPTION OF PREFERRED EMBODIMENTS

Figure 1:
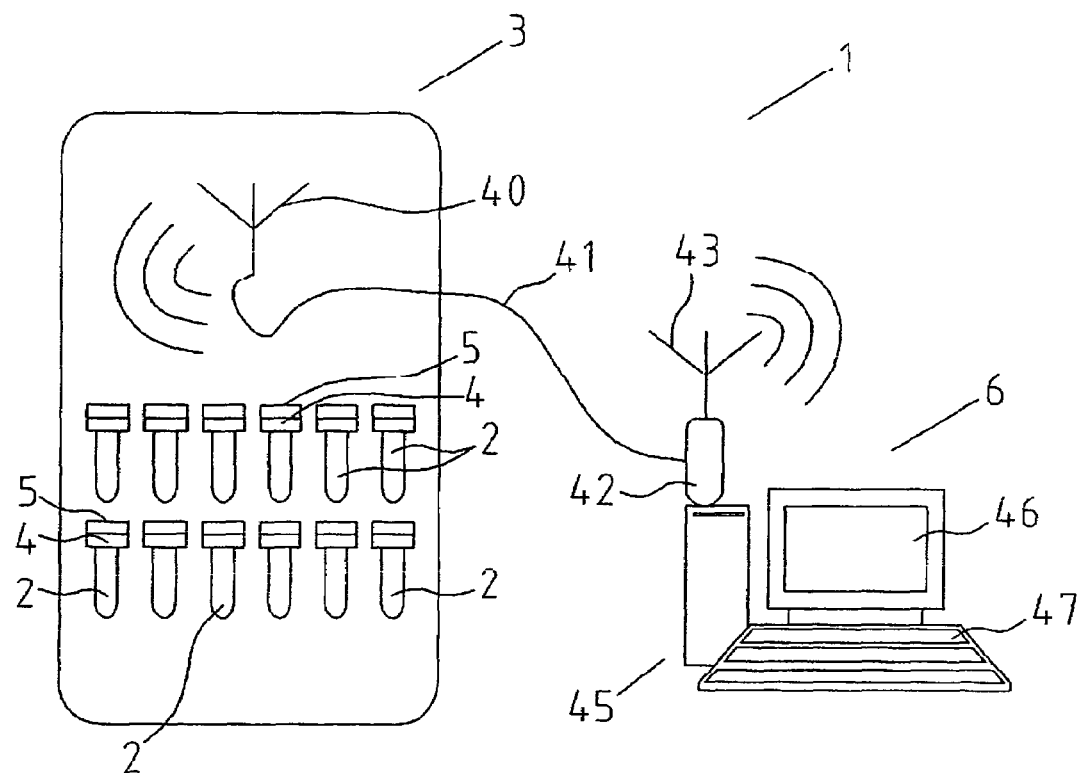
FIG. 1 is a schematic illustration of a material stability test system according to the invention.
Figure 2:
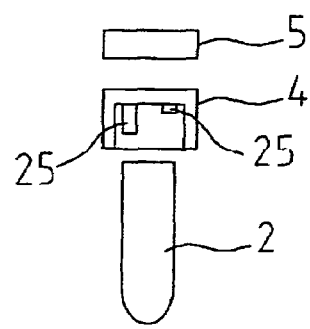
FIG. 2 is an exploded elevational view of a material sample test container forming portion of the system.
Figure 3:
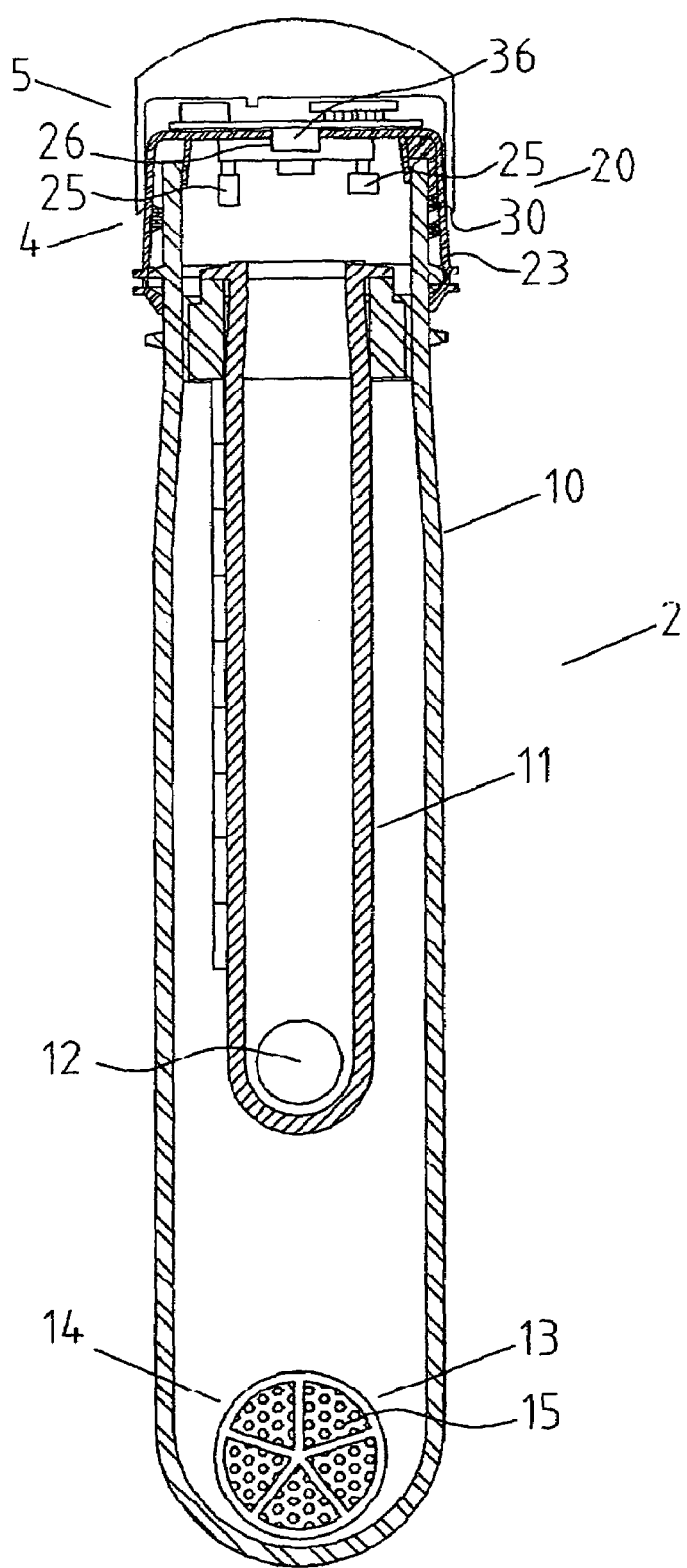
FIG. 3 is an enlarged sectional view of the container.
Figure 4:
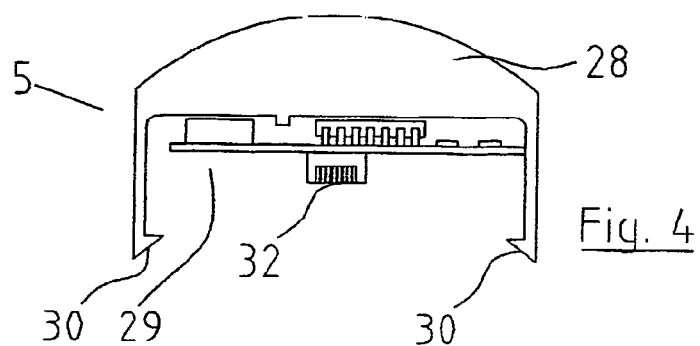
FIG. 4 is an enlarged detail sectional view of a datalogger unit forming portion of the container.
Figure 5:
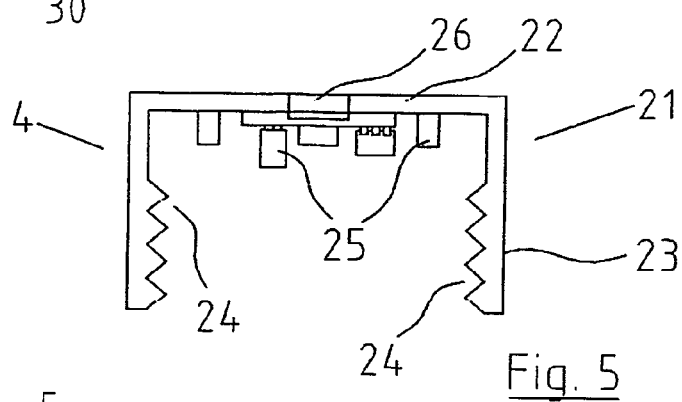
FIG. 5 is an enlarged detail sectional view of a sensor unit forming portion of the container.

Referring to the drawings, there is illustrated a material stability test system according to the invention indicated generally by the reference numeral 1. A system 1 comprises a plurality of sealable test containers 2 which in use are mounted within an associated environmental chamber 3. Each container 2 has means for generating a desired climate condition of humidity within the container 2. This is done in the manner described in our earlier patent application (Publication No. WO 01/31316) the contents of which are incorporated herein by reference. Each container 2 has a cover incorporating a sensor unit 4 for sensing the climate conditions within the container 2 and an associated datalogger unit 5 for collecting sensed information and transmitting said information to a remote monitoring station 6 for recordal and/or display.

Each container 2 is formed of PET (polyethylene teraphthalate) or any other suitable plastics material or other material and is of two-part construction comprising an outer container or flask 10 within which is nested a smaller inner container or test tube 11. A test sample 12 is supported within the test tube 11. A humidifier 13 is mounted within the flask 10 and comprises a cylindrical vial 14 having perforated ends 15 and containing a selected non-saturated salt solution for generating a desired humidity within the flask 10 for carrying out the material stability test on the test sample 12. A screw-on cover 20 is engagable with an upper end of the flask 10 to seal the container 2.

In this case the cover 20 is of two-part construction incorporating the sensor unit 4 and the datalogger unit 5. The sensor unit 4 has a plastics cap body 21 forming an inner cover part having a top 22 with a downwardly depending skirt 23 having threads 24 on an internal bore of the skirt 23 for engagement with associated threads at an upper end of the outer flask 10 of the container 2. Sensors 25 for monitoring temperature and humidity are mounted on an inside face of the top 22 to sense temperature and humidity within the container 2 when the cover 20 is mounted on the container 2. The humidity sensor will typically have an operating range of 0–100% relative humidity with plus or minus 5% accuracy or better. The temperature sensor will have an operating range of 0–70° C. with plus or minus 0.5° C. accuracy or better. The sensor unit 4 also has a calibration data memory. The sensor unit 4 may have a non-volatile memory (EEPROM) to store calibration data for the sensor elements and a unique ID number for the sensor unit 4. A port 26 for connection to the datalogger unit 5 is provided in the top 22.

The datalogger unit 5 has a body 28 forming an outer cover part with a downwardly open socket 29 for reception of the top 22 of the sensor unit 4. An inwardly extending rib 30 at a mouth of the socket 29 engages and grips an exterior of the skirt 23 of the sensor unit 4 to hold the datalogger unit 5 in engagement with the sensor unit 4. The datalogger unit 5 has a processor which is connected to a radio frequency transceiver with associated antenna and a battery power supply. A timing reference and EEPROM storage are also provided. Sufficient non-volatile memory (EEPROM) is included to provide storage for the data, for example two years worth of data, read at 30 minute intervals. It will be noted that the system can be adapted to provide any required data storage using any desired reading interval. The datalogger transceiver will transmit and receive on licence free bands such as 433 and 916 megahertz ISM band, or any other suitable band. Transmissions are initiated in response to commands from the PC 45 and base station 42. An antenna which is included in the datalogger unit 5 has a range of transmission designed to function within the confines of a laboratory bench top environment. A connector 32 engages with the port 26 on the sensor unit 4 for interconnecting the sensor unit 4 and datalogger unit 5. Alternatively it will be noted that the connector 32 may be provided on the sensor unit 4 for co-operation with a port 26 on the datalogger unit 5.

A first antenna 40 is mounted within the environmental chamber 3 to facilitate collection of data from the datalogger units 5 of the containers 2 by radio frequency (RF) link. A hardwire link 41 connects the antenna 40 to an RF base station 42 with antenna 43 located externally of the environmental chamber 3. The monitoring station 6 also includes a PC 45 with display screen 46 and keyboard 47.

It will be appreciated that the containers 2 may in some cases be mounted in an open frame or chamber such as a heating jacket which would allow direct data transmission from the dataloggers 5 to the remote monitoring station 6 without the need for an antenna 40 and hardwire link 41.

In use, each container 2 is prepared by inserting a humidifier 13 into the outer flask 10, loading the sample 12 in the inner test tube 11 and mounting the inner test tube 11 within the outer flask 10. The atmospheres in the outer flask 10 and inner test tube 11 are freely in communication whilst at the same time the test sample 12 and humidifier 13 are kept separate. The sensor unit 4 is screwed onto the outer flask 10 to seal the container 2. The datalogger unit 5 is then mounted on the sensor unit 4, being pressed into position, engaging the connector 32 with the port 26. Upon engagement the datalogger unit 5 will automatically switch on and is ready for communication. The datalogger unit 5 reads the sensor identifier and calibration data and uploads the identifier via the antenna 40 and RF base station 42 to the PC 45 at the monitoring station 6. Then the PC 45 will prompt for sample information requiring an operator to input sample description, batch number and container identification. The PC 45 will acknowledge acceptable information format and will clear all memory in the datalogger 5 and download test set-up to the datalogger 5 and initiate operation of the datalogger 5.

The operation of the datalogger unit 5 involves the datalogger unit 5 remaining in "sleep" mode for the duration of the interval defined in the test set-up (this will typically be about 30 minutes). On completion of this interval, the datalogger unit 5 takes a reading for both temperature and humidity from the sensor unit 4 and processes the readings before storing the data in the EEPROM. Once the data is stored, the datalogger 5 activates the RF link to listen for broadcast instructions. Once the listening period is complete, the datalogger unit 5 returns to "sleep" mode for the next interval or until instructed when to resume listening mode. The datalogger unit 5 will also listen for data upload requests at subdivisions of this interval (e.g. every 10 minutes) depending on the user defined configuration.

The above-mentioned set-up process is repeated for all of the containers 2 within the environmental chamber 3.

In ongoing operation each datalogger unit 5 RF receiver section listens for an instruction at intervals defined in the test set-up. If no instruction is being broadcast the datalogger unit 5 resumes "sleep" mode. If an instruction is being broadcast the datalogger unit receives a marker time for when to listen next. As each datalogger 5 randomly wakes up during the interval period a broadcast instruction is received to resume listening in X seconds for example. At the instructed time the datalogger unit 5 resumes listening mode. At an instructed time and after a predefined interval the monitoring station 6 starts to poll all or selected ones of the datalogger units 5 of the containers 2 within the environmental chamber 3 for stored data. Upon completion of each data upload, the monitoring station 6 instructs the datalogger unit 5 to resume normal operation. If no instruction is broadcast the datalogger unit 5 resumes sleep mode.

Under command from the PC 45 the datalogger 5 will upload the serial number from the sensor EEPROM the software in the datalogger unit 5 will control all aspects of the acquisition, time stamping and storage of the captured data. Any pre-processing e.g. averaging of the data samples will be performed at this stage. An asynchronous algorithm for the transactions with the base station will be employed. Once connection is made to an individual datalogger unit 5 it will remain awake until the complete transaction is finished. The timing of the data capture will be based on a crystal generated clock to ensure integrity of the time interval between the data collection points. Under command from the PC 45 the datalogger unit 5 will upload the stored data to date from the datalogger EEPROM. The previously stored EEPROM data will be retained and cumulatively added to with successive data points. The software at the PC 45 base station will provide the facility to upload data mid-test without compromising the data for the end of test upload. The PC 45 base station can optionally allow the use of a specified bar code reader for data tracking purposes.

It will be appreciated that the system of the invention allows sensing of temperature and humidity within each container 2. For each container 2 the sensed data is stored locally, collected data being stored within the datalogger unit 5. A facility is provided for on demand download of the stored data. An operator can instigate the on demand download at the remote monitoring station 6. Remote readout of the data is possible during tests. Data can be retrieved from each container without disturbing the samples in test.

Each sensor unit 4 has a facility for a unique identifier. The sensor electronics have sufficient storage capability to include a unique identifier number or code for that sensor unit 4.

Ideally a timing reference for the data readings is included. For example this could take the form of a counter facilitating calculations back to identify the time of any particular data point.

Figure 7:
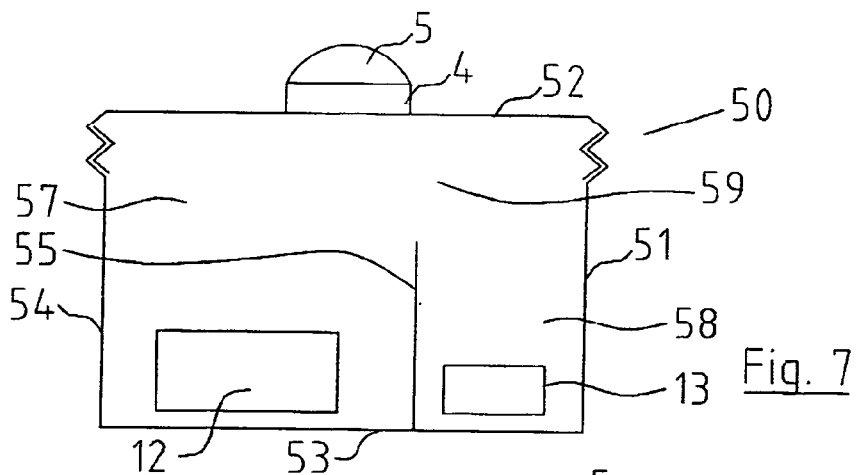
FIG. 7 is a schematic sectional elevational view of another container for use with the system of the invention.

Referring now to FIG. 7 there is illustrated another test container, indicated generally by the reference numeral 50 for use in the system as an alternative to the test container 2 described previously. In this case the container 50 has a plastics container body 51 with an associated screw-on cover 52. This container 51 has a base 53 with an upstanding side wall 54. An internal wall 55 upstanding from the base 53 within the container 51 subdivides the interior of the container 51 into two separate compartments namely a sample compartment 57 and a humidifier compartment 58. It will be noted that the internal wall 55 does not extend upwardly as far as the cover 52, there being a gap or opening 59 between a top of the inner wall 55 and the cover 52 to allow equalisation of the atmospheric conditions within the container 51 throughout the container 51. A sensor unit 4 and associated datalogger unit 5 similar to those previously described are mounted on the cover 52.

In use, a test sample 12 is mounted in the sample compartment 57 of the container 51. A humidifier 13 is mounted within the humidifier compartment 58. After engagement of the cover 52 the humidifier 13 generates a desired humidity within the container 51 as previously described. Climate conditions within the container 51, in particular temperature and humidity, are monitored by the sensor unit 4 and transmitted to the remote monitoring station 6 by the datalogger unit 5.

It will be appreciated that the inner wall 55 could be continued upwardly to meet the cover 52, however with such a construction then through holes would need to be provided in the inner wall 55 to allow humidity to equalise throughout the container 51.

Ideally the container 51 is constructed of plastics material. In this regard, instead of a screw type engagement between the cover 52 and the container body 51 a single piece container 50 may be provided with the cover 52 hingedly connected at one side to an upper end of the side wall 54. It would however be essential to be able to seal the interior of the container 50 when the cover 52 is in a closed position for control of the atmosphere within the container 50. In this regard, the cover 52 and the body 51 of the container 50 may be adapted to seal when the cover 52 is closed. If not, then some other form of sealing means needs to be provided. This could possibly be provided by a sealing tape which extends around the cover 52 between the cover 52 and the upper end of the body 51 of the container 50.

Figure 8:
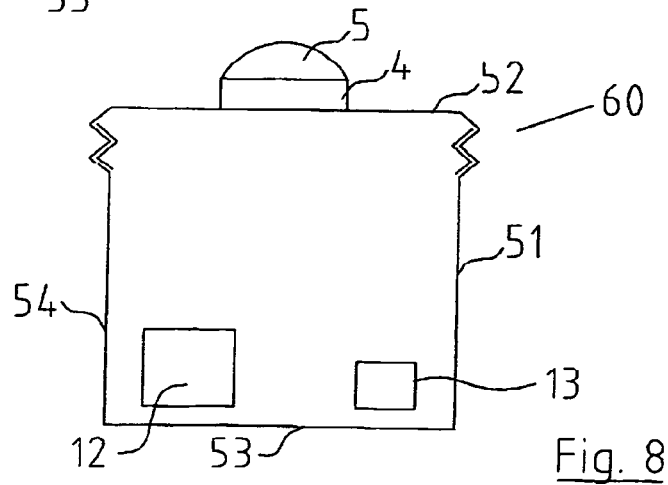
FIG. 8 is a view similar to FIG. 7 of another container for use with the system of the invention.
Figure 6:
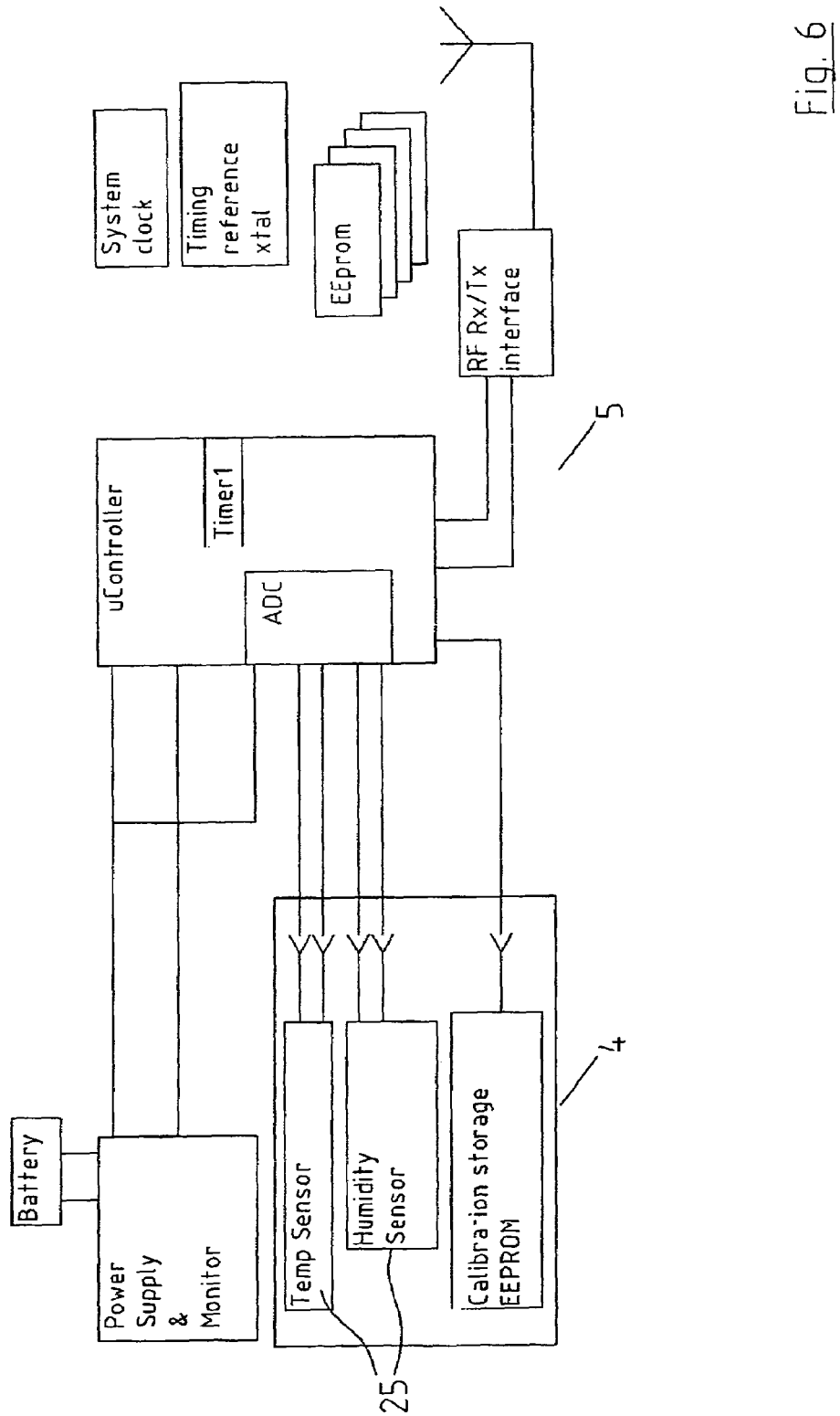
FIG. 6 is a schematic block diagram illustrating the datalogger and sensor electronics.

Referring now to FIG. 8, another test container, indicated generally by the reference numeral 60, is shown. This is largely similar to the container of FIG. 7 and like parts are assigned the same reference numerals. In this case no internal dividing wall is provided within the container body 51 which forms one compartment for reception of both the test sample 12 and the humidifier 13.

It will be noted that the temperature and humidity sensors may be provided separately or both sensors may be integrated in a single sensing element.

While temperature and humidity sensors have been previously mentioned, various other sensors may optionally be provided to sample other critical parameters, such as light, carbon dioxide, and solvents for example.

In a further application of the system a test material is placed and enclosed in a container 2 without any humidifier 13. The relative humidity is monitored at a given temperature (which could be ambient temperature) until an equilibrium is reached. This is called the Equilibrium Relative Humidity or Water Activity. The measurement of this value can give an indication whether at a particular relative humidity a test material will absorb water or lose water to the atmosphere.

It will be appreciated that advantageously the system of the invention allows recordal of very accurate temperature and humidity readings for each individual sample in its own test container. The system of the invention allows the generation of individual humidity and temperature data for each sample rather than taking general readings for a plurality of samples in a humidity cabinet or room as is required and done in the prior art. Further, no controlled-humidity cabinet is required with the system of the present invention. Also, the system is very versatile and a wide range of relative humidity and temperature combinations can be generated in the containers. Further, relative humidity and temperature effects can be studied independently.

While the systems described in the embodiments herein disclose a local radio communication between the containers and the remote monitoring station, various other remote communication systems may be employed such as GSM and SMS systems.

The system can also conveniently be used when shipping product to monitor a sample of the product during shipping. If a problem subsequently arises with the product in use the data recorded can be used to determine whether the deterioration was due to faulty production or due to conditions encountered during shipping.

The datalogger may be provided with the unique identifier number or it may be more convenient to have the computer assign a unique identifier to each datalogger/container at setup.

In the specification the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiments hereinbefore described but may be varied in both construction and detail within the scope of the appended claims.

The invention claimed is:

1. A material stability test system including:
a sealable test container for reception of a test sample of a material to be stability tested,
means for sensing a climate condition within the test container when the test container is sealed in use,
data storage means in communication with the sensing means for recording measured values of said sensed climate condition,
the data storage means being separate from the test container and a data transfer means being provided for communicating the measured values of the sensed climate condition to said remote data storage means,
the sensing means and the data transfer means being mounted on a removable cover of the test container, and
a two-part cover including an inner cover part and an outer cover part being provided for the test container, said inner cover part being engagable with a body of the container to seal the container, the sensing means having sensors which are mounted on an inside face of the inner cover part, the outer cover part being engagable with the inner cover part, the data transfer means being mounted on the outer cover part, a connector being provided on one cover part for complementary engagement with an associated port on the other cover part for interconnecting the sensing means and the data transfer means.

2. The system as claimed in claim 1, further comprising means for generating a desired climate condition provided within the test container.

3. The system as claimed in claim 1, wherein the test container has a data transmitter for transmitting data by a radio signal to the data storage means.

4. The system as claimed in claim 1, wherein the sensing means is demountably engagable with the test container.

5. The system as claimed in claim 1, wherein the data transfer means is demountably engagable with the test container.

6. The system as claimed in claim 1, wherein the inner cover part has a cap body having a top with a downwardly depending skirt having threads on an internal bore of the skirt for engagement with associated threads at an upper end of the test container, the sensors being mounted on an inside face of the top of the cap body.

7. The system as claimed in claim 1, wherein the outer cover part has a body with a downwardly open socket for reception of the top of the cap body of the inner cover part, an inwardly extending rib being provided at a mouth of the socket for engaging and gripping an exterior of the skirt of the cap body to interengage the two cover parts.

8. The system as claimed in claim 1, wherein the data transfer means has a processor which is connected to a radio frequency transceiver with an associated antenna and battery power supply.

9. The system as claimed in claim 1, wherein the sensing means and the data transfer means are mounted on a body of the test container.

10. The system as claimed in claim 1, further comprising means for generating a unique identifier associated with the test container or test sample and means for associating said identifier with the sensed climate condition data prior to communicating the identifier and associated sensed climate condition data together to the data storage means.

11. The system as claimed in claim 1, further comprising an environmental chamber for reception of a plurality of separate test containers, said chamber including means for controlling the temperature within the chamber.

12. The system as claimed in claim 11, further comprising a first internal radio antenna is mounted within the environmental chamber to facilitate collection of data from test containers mounted within the environmental chamber in use, said first radio antenna being connected to an external radio frequency base station located outside the environmental chamber for communication of information between an interior and an exterior of the environmental chamber, said base station having means for communication with the data storage means.

13. A material stability test system comprising:
a sealable test container for reception of a test sample of a material to be stability tested,
means for generating a desired climate condition within the test container,
means for sensing a climate condition within the test container when the test container is sealed in use,
data storage means in communication with the sensing means for recording measured values of said sensed climate condition,
the data storage means being separate from the test container and a data transfer means being provided for communicating the measured values of the sensed climate condition to said remote data storage means,
the sensing means and the data transfer means being mounted on a removable cover of the test container, and
a two-part cover including an inner cover part and an outer cover part being provided for the test container, said inner cover part being engagable with a body of the container to seal the container, the sensing means having sensors which are mounted on an inside face of the inner cover part, the outer cover part being engagable with the inner cover part, the data transfer means being mounted on the outer cover part, a connector being provided on one cover part for complementary engagement with an associated port on the other cover part for interconnecting the sensing means and the data transfer means.

14. The system as claimed in claim 13, wherein the inner cover part has a cap body having a top with a downwardly depending skirt having threads on an internal bore of the skirt for engagement with associated threads at an upper end of the test container, the sensors being mounted on an inside face of the top of the cap body.

15. The system as claimed in claim 13, wherein the outer cover part has a body with a downwardly open socket for reception of the top of the cap body of the inner cover part, an inwardly extending rib being provided at a mouth of the socket for engaging and gripping an exterior of the skirt of the cap body to interengage the two cover parts.

* * * * *